United States Patent
Viola

(10) Patent No.: US 9,220,499 B2
(45) Date of Patent: Dec. 29, 2015

(54) WOUND CLOSURE DEVICE INCLUDING BARBED PINS

(75) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 552 days.

(21) Appl. No.: 12/914,253

(22) Filed: Oct. 28, 2010

(65) Prior Publication Data

US 2012/0109188 A1    May 3, 2012

(51) Int. Cl.
*A61B 17/08*   (2006.01)
*A61B 17/064*  (2006.01)
*A61B 17/06*   (2006.01)
*A61B 19/00*   (2006.01)

(52) U.S. Cl.
CPC ....... *A61B 17/064* (2013.01); *A61B 2017/0609* (2013.01); *A61B 2017/0647* (2013.01); *A61B 2019/306* (2013.01)

(58) Field of Classification Search
CPC ............. A61B 2017/00654; A61B 2017/0609; A61B 17/064; A61B 17/08
USPC ............. 606/75, 99, 104, 139, 142, 153, 219, 606/232; 81/52, 53.2; 411/388–389, 451.1, 411/456
See application file for complete search history.

(56) References Cited

U.S. PATENT DOCUMENTS

| | | | | |
|---|---|---|---|---|
| 71,909 A | * | 12/1867 | Pierce | 411/389 |
| 188,668 A | * | 3/1877 | Pleukharp | 411/389 |
| 549,555 A | * | 11/1895 | White | 411/456 |
| 709,392 A | * | 9/1902 | Brown | 606/221 |
| 816,026 A | * | 3/1906 | Meier | 606/221 |
| 3,166,072 A | * | 1/1965 | Sullivan, Jr. | 606/153 |
| 3,221,746 A | * | 12/1965 | Noble | 606/155 |
| 3,276,172 A | * | 10/1966 | Hjalmar | 52/127.12 |
| 3,494,006 A | * | 2/1970 | Brumlik | 24/447 |
| 3,897,713 A | * | 8/1975 | Gugle | 411/389 |
| 4,015,504 A | * | 4/1977 | Rosan et al. | 411/389 |
| 4,114,624 A | | 9/1978 | Haverstock | |
| 4,647,300 A | | 3/1987 | Sheets | |
| 5,026,385 A | | 6/1991 | Schutte et al. | |

(Continued)

FOREIGN PATENT DOCUMENTS

EP    2156795 A2    2/2010
WO    03/007839 A2    1/2003

OTHER PUBLICATIONS

European Search Report for EP 10177651.6-1526 date of completion is Dec. 14, 2010 (3 pages).

(Continued)

*Primary Examiner* — Gregory Anderson
*Assistant Examiner* — Son Dang

(57) ABSTRACT

A wound closure device includes an elongated body, a depth stop, and one or more barbs. The elongated body has first and second ends. The ends are configured and dimensioned for insertion within tissue on opposed sides of a wound. The depth stop is positioned on the elongated body to limit the insertion depth of at least a portion of the elongated body within tissue. The one or more barbs extend radially from the elongated body and define an inner surface. The inner surface includes a first portion, a second portion, and a third portion. The first portion is disposed at a first orientation relative to a longitudinal axis of the elongated body. The second portion is disposed at a second orientation relative to the longitudinal axis. The third portion disposed at a third orientation relative to the longitudinal axis.

20 Claims, 8 Drawing Sheets

(56) References Cited

U.S. PATENT DOCUMENTS

| | | | |
|---|---|---|---|
| 5,100,391 A | 3/1992 | Schutte et al. | |
| 5,209,755 A | 5/1993 | Abrahan et al. | |
| 5,730,750 A | 3/1998 | Haradon | |
| 5,769,583 A * | 6/1998 | Girbinger | 411/389 |
| 5,797,936 A | 8/1998 | Kleihues | |
| 5,954,723 A * | 9/1999 | Spetzler | 606/309 |
| 6,102,919 A | 8/2000 | Licata | |
| 6,241,747 B1 * | 6/2001 | Ruff | 606/216 |
| 6,620,178 B1 | 9/2003 | Brotz | |
| 7,276,073 B2 | 10/2007 | Adams | |
| 7,374,566 B1 | 5/2008 | Schossan | |
| 7,445,624 B2 | 11/2008 | Freier et al. | |
| 2001/0021861 A1 | 9/2001 | Boebel et al. | |
| 2001/0029386 A1 | 10/2001 | Matsutani et al. | |
| 2002/0077661 A1 | 6/2002 | Saadat | |
| 2003/0032961 A1 * | 2/2003 | Pelo et al. | 606/72 |
| 2004/0010275 A1 * | 1/2004 | Jacobs et al. | 606/153 |
| 2004/0060409 A1 * | 4/2004 | Leung et al. | 83/522.14 |
| 2005/0065542 A1 | 3/2005 | Mansfield | |
| 2006/0095134 A1 * | 5/2006 | Trieu et al. | 623/17.16 |
| 2006/0241663 A1 | 10/2006 | Rice et al. | |
| 2007/0224237 A1 | 9/2007 | Hwang et al. | |
| 2007/0225761 A1 * | 9/2007 | Shetty | 606/219 |
| 2007/0276420 A1 | 11/2007 | Sorensen et al. | |
| 2008/0109021 A1 | 5/2008 | Medoff | |
| 2008/0215079 A1 | 9/2008 | Collins et al. | |
| 2008/0221617 A1 | 9/2008 | Ruff | |
| 2009/0210006 A1 * | 8/2009 | Cohen et al. | 606/232 |
| 2010/0016810 A1 | 1/2010 | Drews et al. | |
| 2010/0049244 A1 * | 2/2010 | Cohen et al. | 606/213 |
| 2010/0211097 A1 | 8/2010 | Hadba et al. | |

OTHER PUBLICATIONS

European Search Report from European Application No. EP 11 25 0761 mailed Sep. 9, 2013 (7 pages).

* cited by examiner

Fig. 1
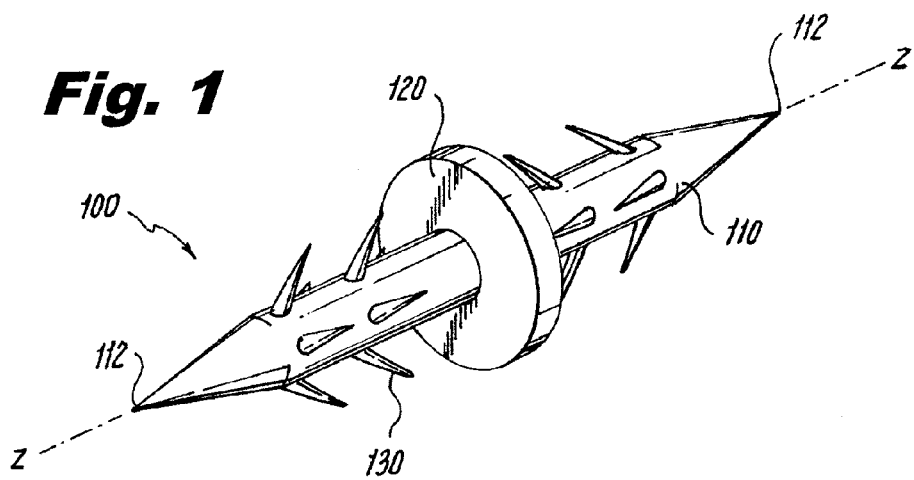
Fig. 1A
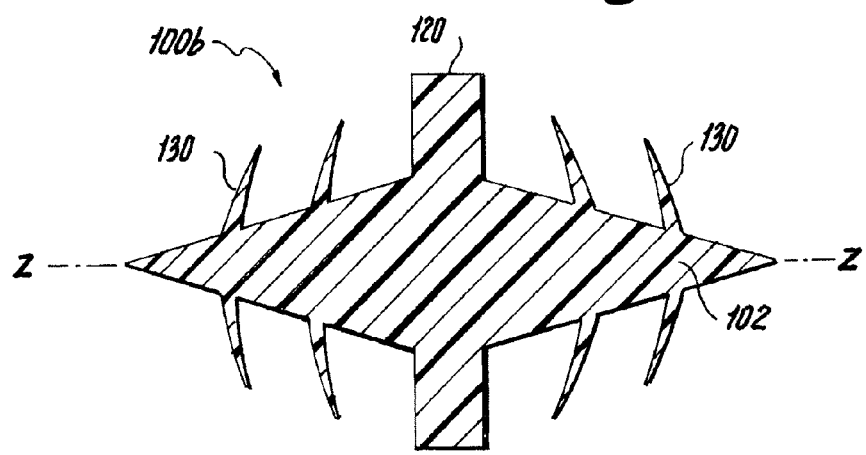
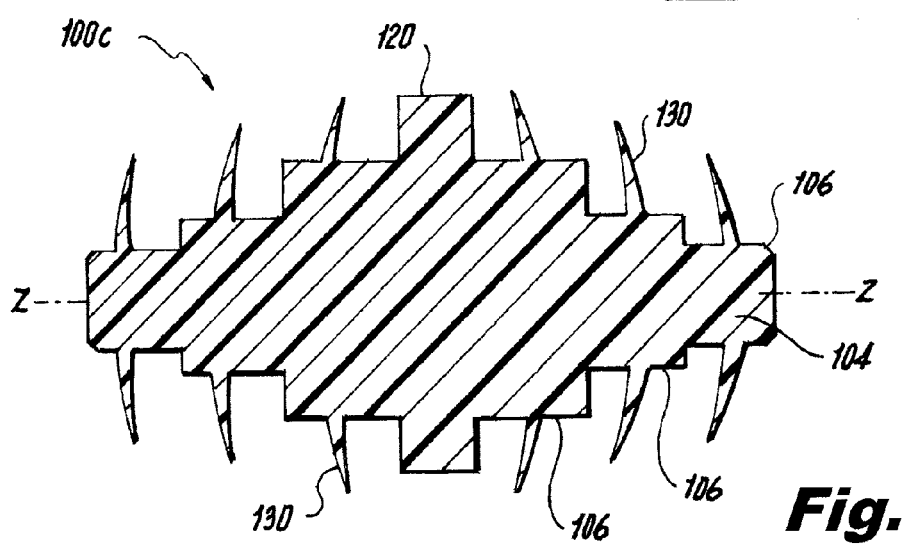
Fig. 1B

Fig. 6
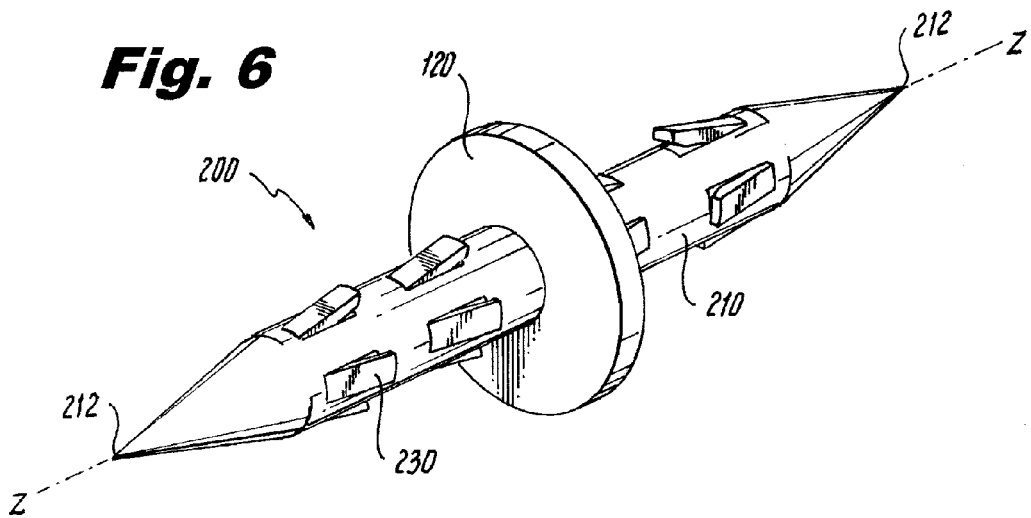
Fig. 7
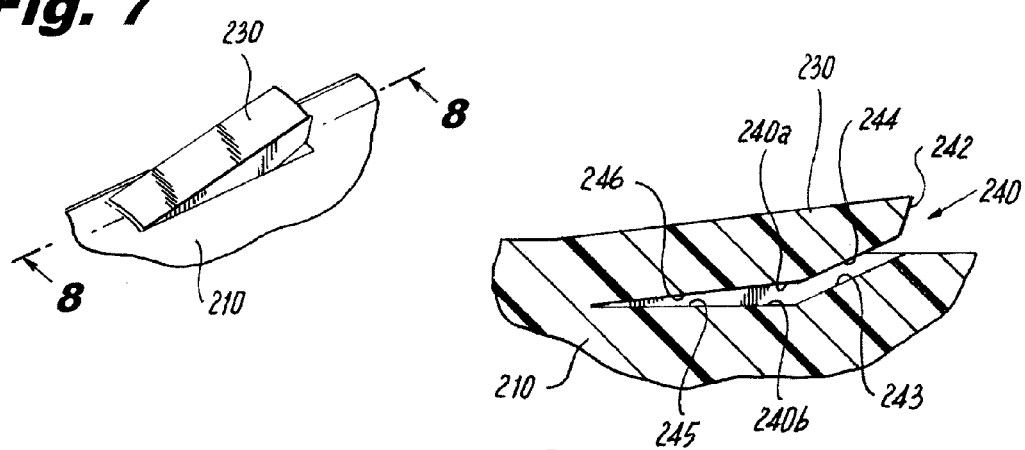
Fig. 8
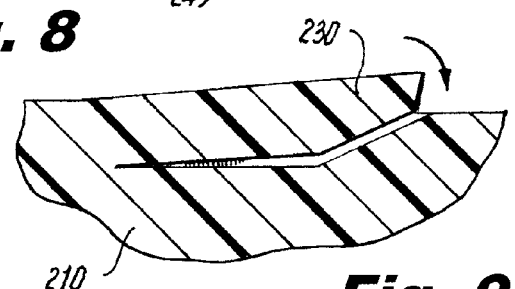
Fig. 9

WOUND CLOSURE DEVICE INCLUDING BARBED PINS

TECHNICAL FIELD

The present disclosure relates generally to incisional hernia prevention. In particular, the present disclosure relates to a medical device for closing a wound that includes one or more barbed pins.

BACKGROUND OF RELATED ART

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic." Throughout the present disclosure, the term "minimally invasive" should be understood to encompass both endoscopic and laparoscopic procedures. In order to complete the procedure, each incision requires closure in order to protect against hernia, adhesions, and other undesirable conditions.

Fastening devices with medical and surgical applications have been described in the prior art. For example, U.S. Patent Application Publication No. 2003/0032961 discloses a double-ended orthopedic tack device having body portions extending from opposing sides of a head portion. The body portions include a threaded portion extending outward from a central body portion. Each body portion may be inserted into opposing bone or tissue structure. In another example, U.S. Pat. No. 6,620,178 discloses a blood vessel grafting aid for joining two blood vessels together. In one embodiment, the blood vessel grafting aid includes a shaft with a centrally positioned plate thereon and a plurality of prongs extending from the shaft to engage into the vessels. In yet another example, U.S. Patent Application Publication No. 2010/0049244 discloses a threaded tissue tack for use in approximating and securing a pair of tissue sections together. The threaded tissue tack has a central body portion and first and second screws extending from opposite ends of the central body portion.

While these previous disclosures teach medical fastening devices, some of which are particularly used for tissue approximation, a continuing need exists for a device that enables a surgeon to securely close an open wound with relative ease and with minor inconvenience.

SUMMARY

Accordingly, a wound closure device is provided which includes an elongated body, a depth stop, and one or more barbs. The depth stop is positioned on the elongated body to limit the insertion depth of at least a portion of the elongated body within tissue. The one or more barbs extend radially outward from the elongated body. The elongated body may include a plurality of barbs formed along at least a portion of a length thereof. One or more of the elongated body, the depth stop, and the one or more barbs comprises a material selected from the group consisting of absorbable materials, non-absorbable materials, and combinations thereof.

The elongated body has first and second sections. The sections are configured and dimensioned for insertion within tissue on opposed sides of a wound. In embodiments, the one or more barbs include an inner surface having one or more inflection points. The inner surface may include one or more concave portions and/or one or more convex portions.

The one or more barbs may be movable between first and second positions. The one or more barbs include a distal tip. In the first position, the distal tip is in close cooperative alignment with the elongated body. In the second position, the distal tip is radially offset from the elongated body.

The one or more barbs define an inner surface. The inner surface includes a first portion, a second portion, and a third portion. The first portion may be disposed at a first orientation relative to a longitudinal axis of the elongated body. The second portion may be disposed at a second orientation relative to the longitudinal axis. The third portion may be disposed at a third orientation relative to the longitudinal axis. One or more of the first, second, and third portions may be substantially linear. The first, second, and third portions may be at first, second, and third angles relative to respective longitudinal axes of the elongated body. In embodiments, the second angle may be less than each of the first and third angles. The first angle may be about 0 degrees to about 90 degrees. In one embodiment, the first angle is about 30 degrees to about 50 degrees. The second angle may be about 0 degrees to about 90 degrees. In one embodiment, the second angle is about 2 degrees to about 25 degrees. The third angle is about 0 degrees to about 90 degrees. In one embodiment, the third angle is about 25 degrees to about 50 degrees.

One or more of the first, second, and third portions may be substantially non-linear. In embodiments, one of the first, second, and third portions is arcuate. In embodiments, one of the first, second, and third portions may be substantially linear and one or more of the first, second, and third portions may be arcuate.

According to another aspect, the wound closure device includes an elongated body and one or more barbs extending radially outward from the elongated body. The elongated body has first and second sections. The sections are configured and dimensioned for insertion within tissue on opposed sides of a wound. The one or more barbs define an inner surface having a first portion disposed at a first orientation relative to a longitudinal axis of the elongated body and a second portion disposed at a second orientation relative to the longitudinal axis.

In yet another aspect, a wound closure device includes an elongated body and first and second barbs extending substantially radially outwardly from the elongated body. The elongated body has first and second sections that are configured and dimensioned for insertion within tissue on opposed sides of a wound. One of the first and second barbs has either more flexibility or more rigidity than the other of the first and second barbs. The first barb may be formed of a first material and the second barb may be formed of a second material different than the first material, each material having either more flexibility or more rigidity than the other of the first and second material. In one embodiment, the first and second barbs have different geometries. The first and second barbs may have different thicknesses and/or depths. One or both of the first and second barbs may have one or more surface treatments. One or both of the first and second barbs may have additional cross-linking.

BRIEF DESCRIPTION OF THE DRAWINGS

Various embodiments of the present disclosure will be described herein below with reference to the figures wherein:

FIG. 1 is a perspective view of one embodiment of a wound closure device in accordance with the principles of the present disclosure;

FIG. 1A is a side cross-sectional view of another embodiment of a wound closure device in accordance with the principles of the present disclosure;

FIG. 1B is a side cross-sectional view of yet another embodiment of a wound closure device in accordance with the principles of the present disclosure;

FIG. 6 is a perspective view of another embodiment of wound closure device in accordance with the present disclosure;

FIG. 7 is perspective view illustrating one embodiment of a barb of the wound closure device of FIG. 6;

FIG. 8 is a side cross-sectional view of the barb shown in FIG. 7, the barb being illustrated in a first position;

FIG. 9 is a side cross-sectional view of the barb shown in FIG. 7, the barb being illustrated in a second position;

DETAILED DESCRIPTION

Figure 2:
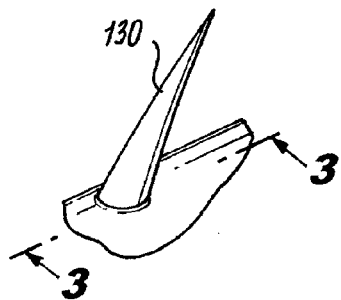
FIG. 2 is perspective view illustrating one embodiment of a barb of the wound closure device of FIG. 1.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Figure 5:
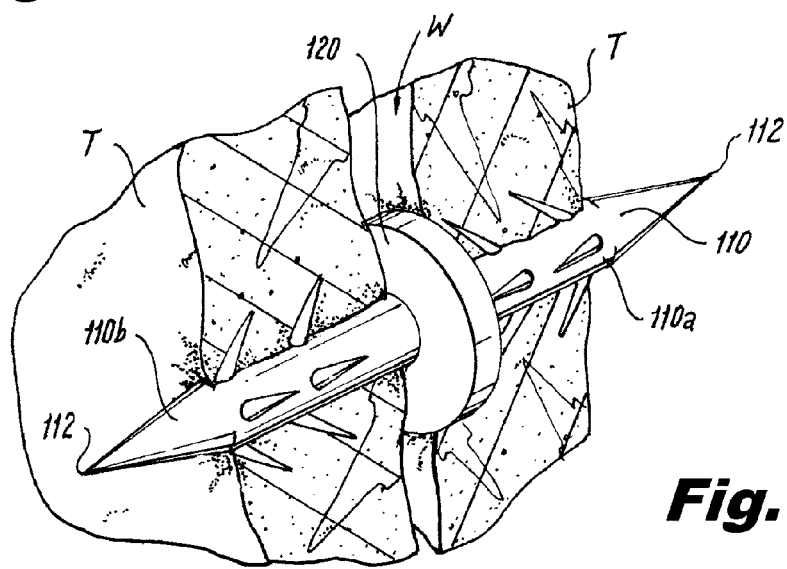
FIG. 5 is a perspective view illustrating the wound closure device of FIG. 1 positioned within tissue.

Referring now to FIG. 1, one embodiment of a wound closure device is illustrated which is generally referred to as 100. Wound closure device 100 includes an elongated body 110, a depth stop 120, and one or more barbs 130. The elongated body 110 defines a longitudinal axis "Z" and includes a pointed tip 112 on each end thereof. As best shown in FIG. 5, the depth stop 120 is positioned on the elongated body 110 to limit the insertion depth of at least a portion of the elongated body 110 within tissue "T." The depth stop 120 further separates the opposing sections of the elongated body 110. The one or more barbs 130 extend from the elongated body 110. The elongated body 110 may include a plurality of barbs 130 formed along at least a portion of a length thereof. One or more barbs 130 may be formed projecting from the elongated body 110 toward one end, while one or more barbs 130 may be projecting from the elongated body 110 toward the other end so as to form a bi-directional wound closure device 100 as generally illustrated in FIG. 1. Generally, the tips of the one or more barbs are oriented towards depth stop 120. Alternatively, a plurality of axially spaced barbs may be formed in the same or random configuration and/or at different angles in relation to each other. Optionally, the wound closure device 100 may include a plurality of barbs spaced at the same and/or different lengths and/or in specified and/or random patterns according to the type of tissue being manipulated and/or procedure performed (not shown). The elongated body 110, the depth stop 120, and/or the one or more barbs 130 may include absorbable materials, non-absorbable materials, and combinations thereof.

Referring now to FIGS. 1A and 1B, show alternate embodiments of wound closure devices in which the diameters of the elongate bodies thereof may have fluctuating diameters. FIG. 1A illustrates a wound closure device 100b having an elongate body 102 that has a diameter which changes along the length of the longitudinal axis "z." More specifically, the diameter gradually increases toward the middle, or depth stop, and then gradually decrease toward both ends thereof. FIG. 1B illustrates a wound closure device 100c that has an elongate body 104 that has a diameter which changes along the length of the longitudinal axis "z," more specifically, the diameter comprises a series of steps 106 therealong the longitudinal axis. The steps 106 comprise smaller diameters near the ends thereof and larger diameters near the middle, or depth stop.

With continued reference to FIGS. 1 and 5, the elongated body 110 has first and second ends 110a, 110b. The ends 110a, 110b are configured and dimensioned for insertion within tissue "T" on opposed sides of a wound "W."

Figure 3:
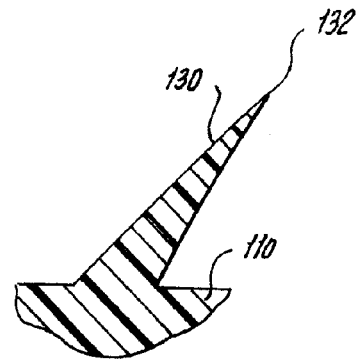
FIG. 3 is a side cross-sectional view of the barb shown in FIG. 2, the barb being illustrated in a first position.
Figure 4:
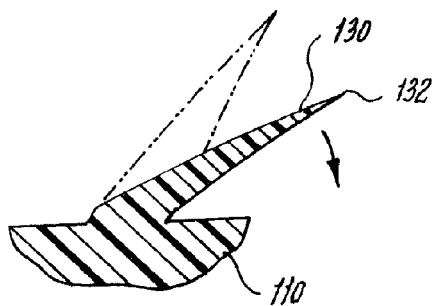
FIG. 4 is a side cross-sectional view of the barb shown in FIG. 2, the barb being illustrated in a second position.

As illustrated in FIGS. 3 and 4, the one or more barbs 130 may be movable between first and second positions. The one or more barbs 130 include a distal tip 132. In one position, the distal tip 132 is in close cooperative alignment with the elongated body 110 (FIG. 4). In another position, the distal tip 132 is radially offset from the elongated body 110 (FIG. 3).

Referring now to FIGS. 6-10, another embodiment of a wound closure device is illustrated and is generally referred to as 200. Wound closure device 200 is similar to wound closure device 100 and will be described herein to the extent necessary to describe the differences in construction and operability thereof. Wound closure device 200 includes an elongated body 210, a depth stop 120, and one or more barbs 230. The elongated body 210 defines a longitudinal axis "Z" and includes a pointed tip 212 on each end thereof. Each of the one or more barbs 230 defines an inner surface 240. The inner surface 240 of the one or more barbs 230 has top and bottom sections 240a, 240b. The top section 240a includes a first portion 242, a second portion 244, and a third portion 246. The bottom section 240b includes a first portion 243 and a second portion 245. The top and bottom sections 240a, 240b may include complementary mating surfaces.

With regards to the top section 240a, the first portion 242 may be disposed at a first orientation relative to the longitudinal axis "Z" of the elongated body 210. The second portion 244 may be disposed at a second orientation relative to the longitudinal axis "Z." The third portion 246 may be disposed at a third orientation relative to the longitudinal axis "Z." Similarly, with regards to the bottom section 240b, the first portion 243 may be disposed at a first orientation relative to the longitudinal axis "Z" and the second portion 245 may be disposed at a second orientation relative to the longitudinal axis "Z." One or more of the orientations may be similar, different, and/or identical. In certain embodiments, top section 240a includes only a first and second portion, 242, and 244 respectively.

Figure 10:
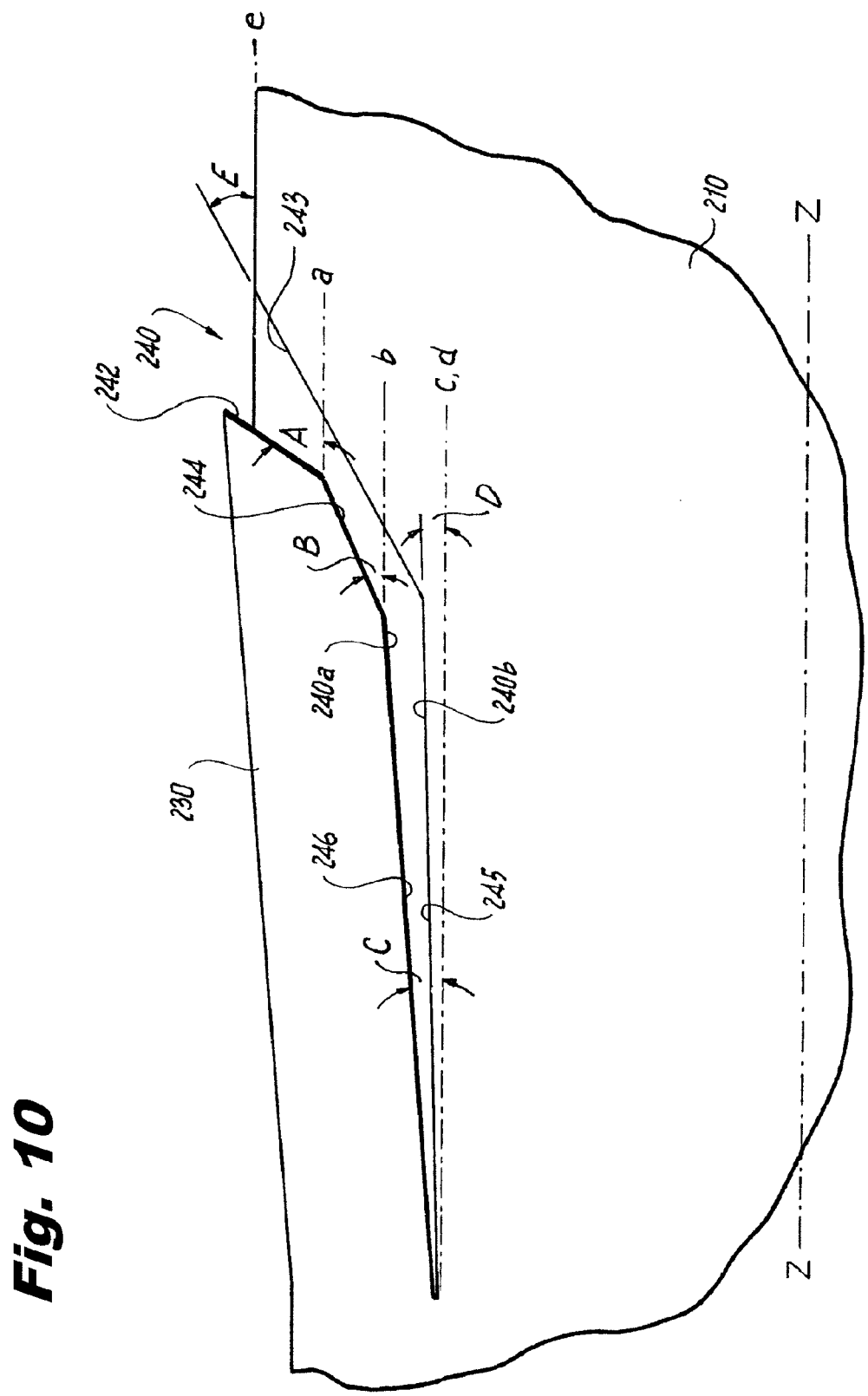
FIG. 10 is an enlarged side view of the barb of FIG. 7.

In this manner, the first, second and/or third portions 242, 244, 246 may be at first, second, and third angles relative to the longitudinal axis "Z" of the elongated body 210. Similarly, the first and second portions 243, 245 may be at fourth and fifth angles relative to the longitudinal axis "Z" of the elongated body 210. As illustrated in FIG. 10, these angles, illustrated by characters A-E relative to respective longitudinal axes a-e may each be about 0 degrees to about 90 degrees (longitudinal axes a-e are parallel to the longitudinal axis "Z" of the elongated body 210). In embodiments, one or more of the angles are about 30 degrees to about 40 degrees. In embodiments, one or more of the angles are about 2 degrees to about 10 degrees.

One or more of the first, second, and third portions 242, 244, 246 may be substantially linear and/or non-linear. Similarly, one or both of the first and second portions 243, 245 may be substantially linear and/or non-linear. In embodiments, one or more of the first, second, and third portions 242, 244, 246 may be arcuate. Similarly, one or both of the first and second portions 243, 245 may be arcuate. In embodiments, one or more of the first, second, and third portions 242, 244, 246 may include one or more inflection points and/or one or more concave and/or convex portions. Similarly, one or both of the first and second portions 243, 245 may include one or more inflection points and/or one or more concave and/or convex portions.

Figure 11:
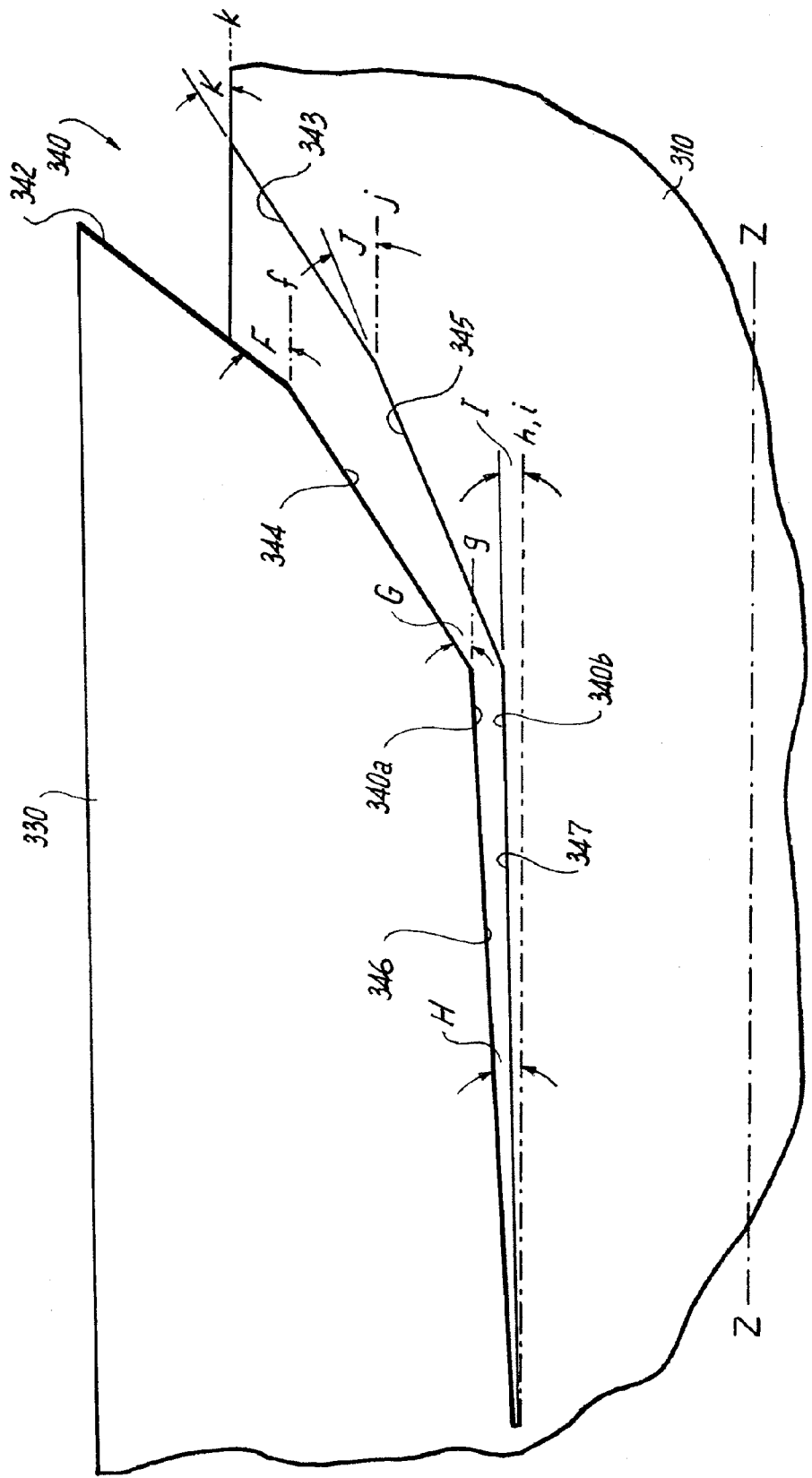
FIG. 11 is an enlarged side view of another embodiment of a barb of the wound closure device of FIG. 6.

Referring now to FIG. 11, another embodiment of a barb is generally referred to as 330. Barb 330 is similar to barb 230 and will be described herein to the extent necessary to describe the differences in construction and operability thereof. Barb 330 defines an inner surface 340. The inner surface 340 of barb 330 has top and bottom sections 340a, 340b. The top section 340a includes a first portion 342, a second portion 344, and a third portion 346. The bottom section 340b includes a first portion 343, a second portion 345, and a third portion 347. The top and bottom sections 340a, 340b may include complementary mating surfaces.

With regards to the top section 340a, the first portion 342 may be disposed at a first orientation relative to the longitudinal axis "Z" of the elongated body 210. The second portion 344 may be disposed at a second orientation relative to the longitudinal axis "Z." The third portion 346 may be disposed at a third orientation relative to the longitudinal axis "Z." Similarly, with regards to the bottom section 340b, the first portion 343 may be disposed at a first orientation relative to the longitudinal axis "Z." The second portion 345 may be disposed at a second orientation relative to the longitudinal axis "Z." The third portion 347 may be disposed at a third orientation relative to the longitudinal axis "Z." One or more of the orientations may be similar, different, and/or identical.

In this manner, the first, second and/or third portions 342, 344, 346 may be at first, second, and third angles relative to respective longitudinal axes of the elongated body 210. Similarly, the first, second, and third portions 343, 345, 347 may be at fourth, fifth, and sixth angles relative to the longitudinal axis "Z" of the elongated body 210. As illustrated in FIG. 11, these angles, illustrated by characters F-K relative to respective longitudinal axes f-k may each be about 0 degrees to about 90 degrees (longitudinal axes f-k are parallel to the longitudinal axis "Z" of the elongated body 210). In embodiments, one or more of the angles are about 30 degrees to about 50 degrees. In embodiments, one or more of the angles are about 2 degrees to about 25 degrees.

One or more of the first, second, and third portions 342, 344, 346 may be substantially linear and/or non-linear. Similarly, one or more of the first, second, and third portions 343, 345, 347 may be substantially linear and/or non-linear. In embodiments, one or more of the first, second, and third portions 342, 344, 346 may be arcuate. Similarly, one or more of the first, second, and third portions 343, 345, 347 may be arcuate. In embodiments, one or more of the first, second, and third portions 342, 344, 346 may include one or more inflection points and/or one or more concave and/or convex portions. Similarly, one or more of the first, second, and third portions 343, 345, 347 may include one or more inflection points and/or one or more concave and/or convex portions.

Figure 12:
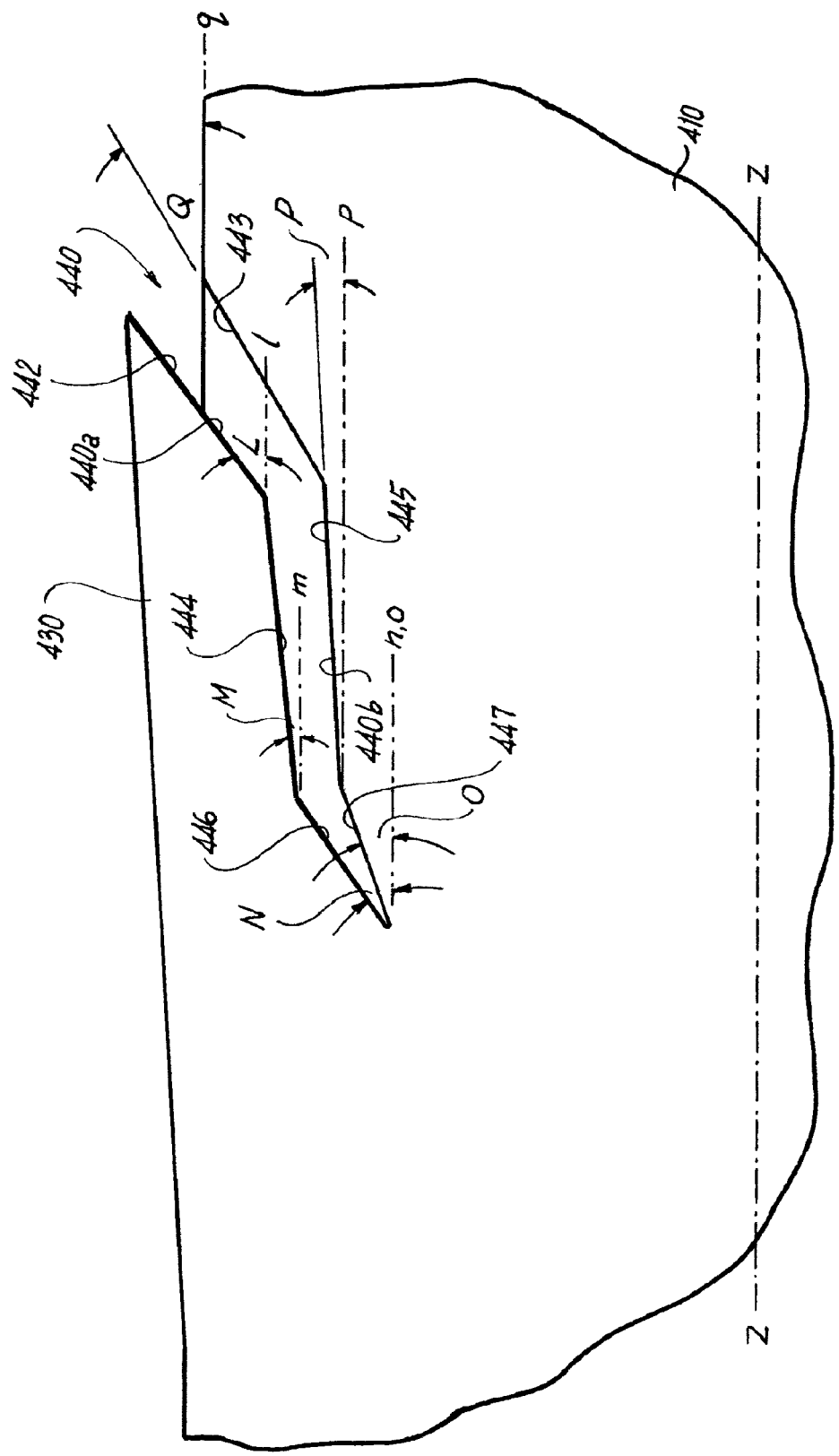
FIG. 12 is an enlarged side view of yet another embodiment of a barb of the wound closure device of FIG. 6.

Referring now to FIG. 12, another embodiment of a barb is generally referred to as 430. Barb 430 is similar to barb 230 and will be described herein to the extent necessary to describe the differences in construction and operability thereof. Barb 430 defines an inner surface 440. The inner surface 440 of barb 430 has top and bottom sections 440a, 440b. The top section 440a includes a first portion 442, a second portion 444, and a third portion 446. The bottom section 440b includes a first portion 443, a second portion 445, and a third portion 447. The top and bottom sections 440a, 440b may include complementary mating surfaces.

With regards to the top section 440a, the first portion 442 may be disposed at a first orientation relative to the longitudinal axis "Z" of the elongated body 210. The second portion 444 may be disposed at a second orientation relative to the longitudinal axis "Z." The third portion 446 may be disposed at a third orientation relative to the longitudinal axis "Z." Similarly, with regards to the bottom section 440b, the first portion 443 may be disposed at a first orientation relative to the longitudinal axis "Z." The second portion 445 may be disposed at a second orientation relative to the longitudinal axis "Z." The third portion 447 may be disposed at a third orientation relative to the longitudinal axis "Z." One or more of the orientations may be similar, different, and/or identical.

In this manner, the first, second and/or third portions 442, 444, 446 may be at first, second, and third angles relative to respective longitudinal axes of the elongated body 410. Similarly, the first, second, and third portions 443, 445, 447 may be at fourth, fifth, and sixth angles relative to the longitudinal axis "Z" of the elongated body 210. As illustrated in FIG. 12, these angles, illustrated by characters L-Q relative to respective longitudinal axes l-q, may each be about 0 degrees to about 90 degrees (longitudinal axes l-q are parallel to the longitudinal axis "Z" of the elongated body 210). In embodiments, one or more of the angles are about 30 degrees to about 50 degrees. In embodiments, one or more of the angles are about 2 degrees to about 25 degrees.

One or more of the first, second, and third portions 442, 444, 446 may be substantially linear and/or non-linear. Similarly, one or more of the first, second, and third portions 443, 445, 447 may be substantially linear and/or non-linear. In embodiments, one or more of the first, second, and third portions 442, 444, 446 may be arcuate. Similarly, one or more of the first, second, and third portions 443, 445, 447 may be arcuate. In embodiments, one or more of the first, second, and third portions 442, 444, 446 may include one or more inflection points and/or one or more concave and/or convex portions. Similarly, one or more of the first, second, and third portions 443, 445, 447 may include one or more inflection points and/or one or more concave and/or convex portions.

Figure 13:
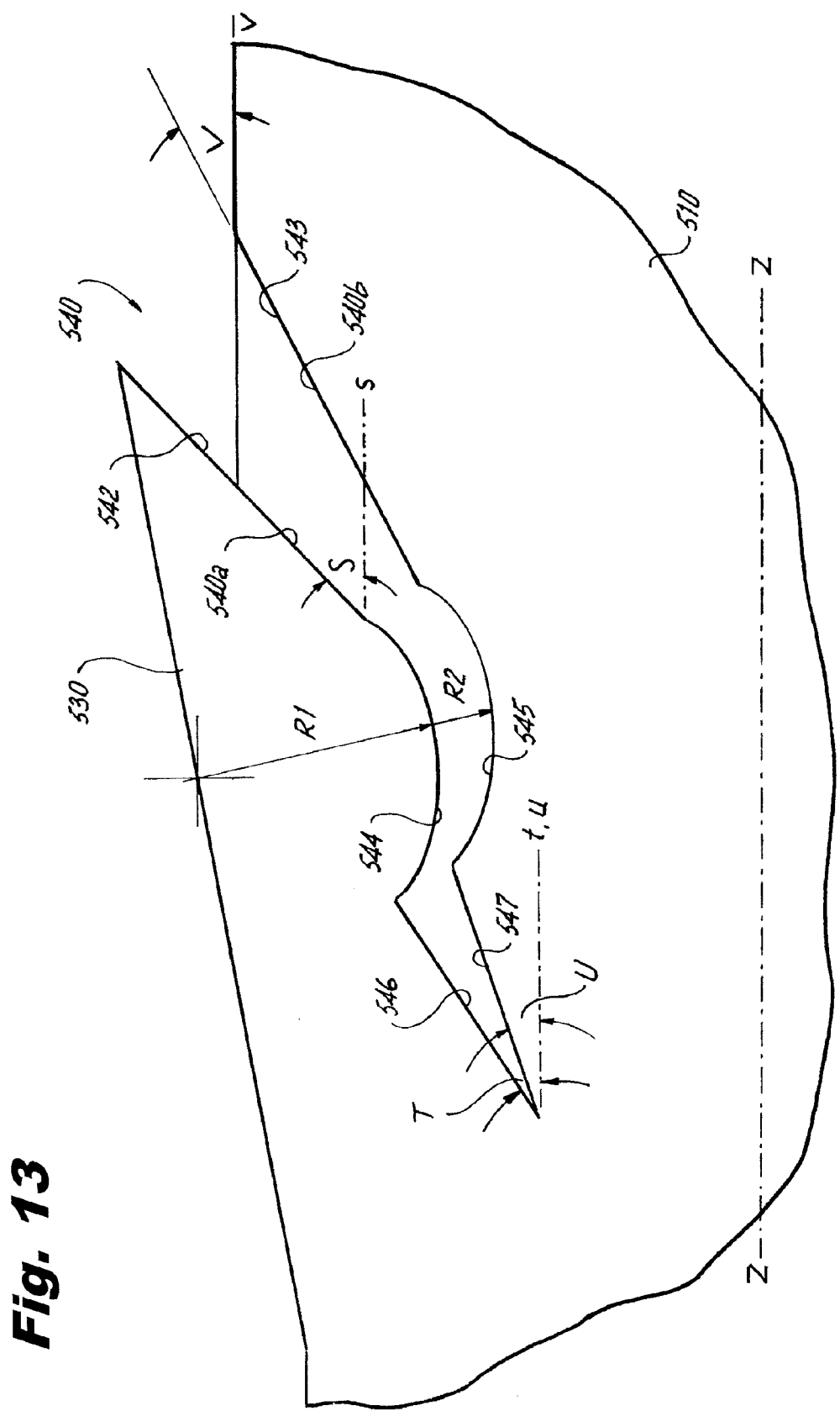
FIG. 13 is an enlarged side view of another embodiment of a barb of the wound closure device of FIG. 6.

Referring now to FIG. 13, another embodiment of a barb is generally referred to as 530. Barb 530 is similar to barb 230 and will be described herein to the extent necessary to describe the differences in construction and operability thereof. Barb 530 defines an inner surface 540. The inner surface 540 of the barb 530 has top and bottom sections 540a, 540b. The top section 540a includes a first portion 542, a second portion 544, and a third portion 546. The bottom section 540b includes a first portion 543, a second portion 545, and a third portion 547. The top and bottom sections 540a, 540b may include complementary mating surfaces.

With regards to the top section 540a, the first portion 542 may be disposed at a first orientation relative to the longitudinal axis "Z" of the elongated body 210. The second portion 544 may be disposed at a second orientation relative to the longitudinal axis "Z." The third portion 546 may be disposed at a third orientation relative to the longitudinal axis "Z." Similarly, with regards to the bottom section 540b, the first portion 543 may be disposed at a first orientation relative to the longitudinal axis "Z." The second portion 545 may be disposed at a second orientation relative to the longitudinal axis "Z." The third portion 547 may be disposed at a third orientation relative to the longitudinal axis "Z." One or more of the orientations may be similar, different, and/or identical.

In this manner, the first, second and/or third portions 542, 544, 546 may be at first, second, and third angles relative to respective longitudinal axes of the elongated body 510. Similarly, the first, second, and third portions 543, 545, 547 may be at fourth, fifth, and sixth angles relative to the longitudinal axis "Z" of the elongated body 210. As illustrated in FIG. 13, characters S-V illustrate one or more of these angles relative to respective longitudinal axes s-v. Each angle may be about 0 degrees to about 90 degrees (longitudinal axes s-v are parallel to the longitudinal axis "Z" of the elongated body 210). In embodiments, one or more of the angles are about 30 degrees to about 50 degrees. In embodiments, one or more of the angles are about 2 degrees to about 25 degrees.

One or more of the first, second, and third portions 542, 544, 546 may be substantially linear and/or non-linear. Similarly, one or more of the first, second, and third portions 543, 545, 547 may be substantially linear and/or non-linear. One or more of the first, second, and third portions 542, 544, 546 may be arcuate. Similarly, one or more of the first, second, and third portions 543, 545, 547 may be arcuate. For example, second portion 544 and second portion 545 have radii of curvature illustrated by respective first and second radii designated R1 and R2. In embodiments, one or more of the first, second, and third portions 542, 544, 546 may include one or more inflection points and/or one or more concave and/or convex portions. Similarly, one or more of the first, second, and third portions 543, 545, 547 may include one or more inflection points and/or one or more concave and/or convex portions.

Figure 14:
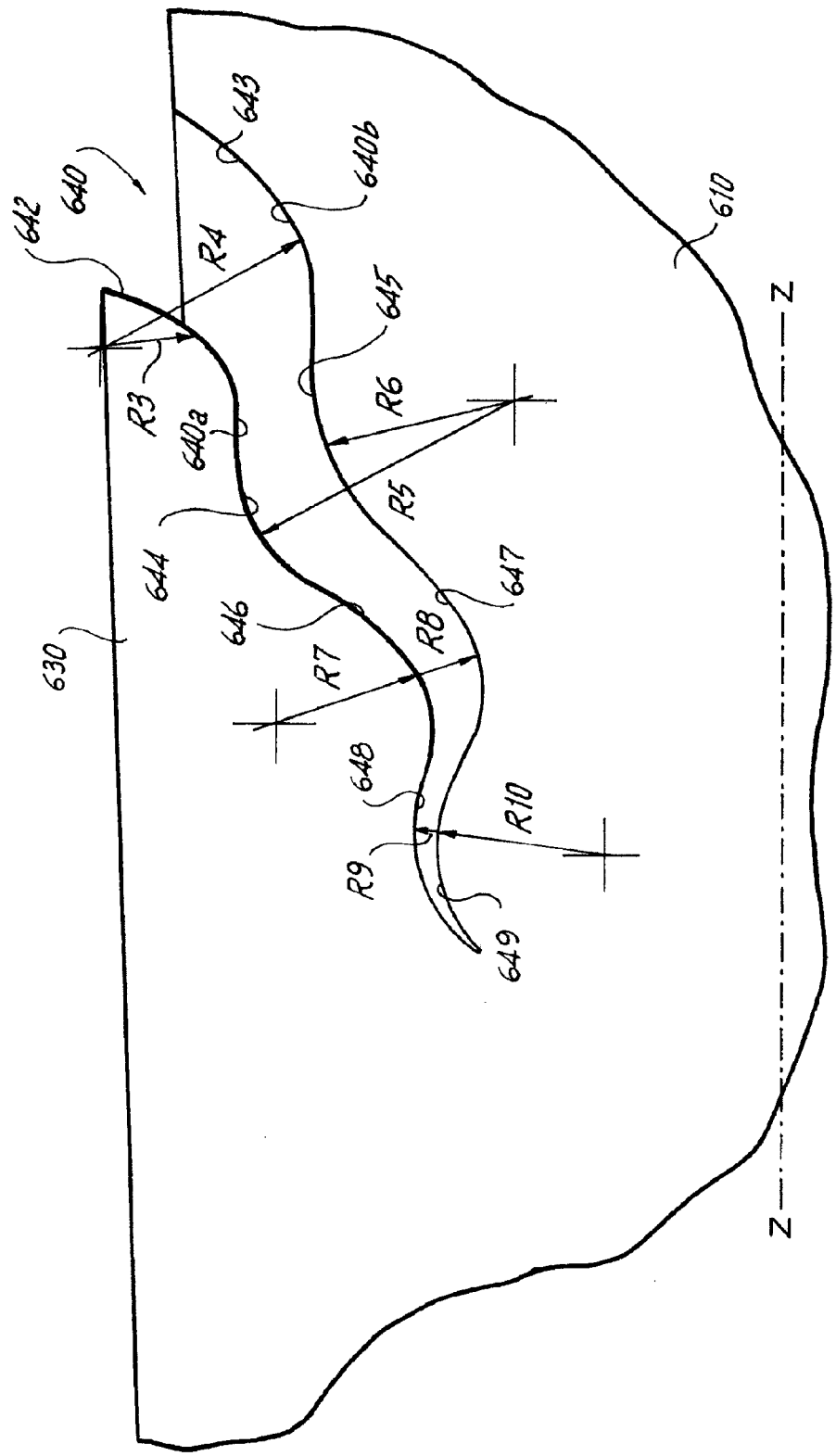
FIG. 14 is an enlarged side view of yet another embodiment of a barb of the wound closure device of FIG. 6.

Referring now to FIG. 14, another embodiment of a barb is generally referred to as 630. Barb 630 is similar to barb 230 and will be described herein to the extent necessary to describe the differences in construction and operability thereof. Barb 630 defines an inner surface 640. The inner surface 640 of barb 630 has top and bottom sections 640a, 640b. The top and bottom sections 640a, 640b may include complementary mating surfaces.

The top and bottom sections 640a, 640b may be substantially linear and/or non-linear. As illustrated in FIG. 14, one or both of the top and bottom sections 640a, 640b may include one or more arcuate portions such as arcuate portions 642, 643, 644, 645, 646, 647, 648, and 649 having radii of curvature R3, R4, R5, R6, R7, R8, R9, and R10, respectively. One or more of the arcuate portions 542, 544, 546 may include one or more inflection points and/or one or more concave and/or convex portions.

In embodiments, the barbs may be arranged on a first portion of a length of the elongated body to allow movement of a first end of the wound closure device through tissue in one direction, while barbs on a second portion of the length of the elongated body may be arranged to allow movement of the second end of the wound closure device in an opposite direction.

The barbs can be arranged in any suitable pattern, for example, helical, linear, or randomly spaced. The pattern may be symmetrical or asymmetrical. The number, configuration, spacing and surface area of the barbs can vary depending upon the tissue in which the wound closure device is used, as well as the composition and geometry of the material utilized to form the wound closure device. Additionally, the proportions of the barbs may remain relatively constant while the overall length of the barbs and the spacing of the barbs may be determined by the tissue being connected. For example, if the wound closure device is to be used to connect the edges of a wound in skin or tendon, the barbs may be made relatively short and more rigid to facilitate entry into this rather firm tissue. Alternatively, if the wound closure device is intended for use in fatty tissue, which is relatively soft, the barbs may be made longer and spaced further apart to increase the ability of the wound closure device to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a wound closure device is used in tissue repair with differing layer structures. In particular embodiments, a single directional wound closure device may have both large and small barbs; in other embodiments a bi-directional wound closure device may have both large and small barbs.

In addition, barbs of the present disclosure may have various stiffness and/or flexibility. For example, some barbs may be rigid while others are flexible. In this respect, the geometry may be varied such as altering the thickness and/or depth and/or shape of some of the barbs. Furthermore, the barbs may have various surface treatments and/or include additional and/or limited amounts of cross-linking in order to alter the flexibility and/or rigidity of one or more of the presently disclosed barbs. In alternate embodiments, some barbs comprise a surface treatment, such as a coating to increase the rigidity. Barb flexibility and rigidity can also be controlled by controlled parameters such as barb thickness and length. Barbs which are thicker and/or shorter are more rigid compared to barbs which are thinner and/or longer.

The wound closure devices in accordance with the present disclosure may be formed of absorbable materials, non-absorbable materials, and combinations thereof. More particularly, the wound closure devices may be formed of an absorbable material selected from the group consisting of polyesters, polyorthoesters, polymer drugs, polyhydroxybutyrates, dioxanones, lactones, proteins, cat gut, collagens, carbonates, homopolymers thereof, copolymers thereof, and combinations thereof. In other embodiments, suitable absorbable materials which may be utilized to form the wound closure device include natural collagenous materials or synthetic resins including those derived from alkylene carbonates such as trimethylene carbonate, tetramethylene carbonate, and the like, caprolactone, glycolic acid, lactic acid, glycolide, lactide, homopolymers thereof, copolymers thereof, and combinations thereof. In some embodiments, glycolide and lactide based polyesters, especially copolymers of glycolide and lactide, may be utilized to form the wound closure device of the present disclosure.

Barbed wound closure devices fabricated from an absorbable material in accordance with the present disclosure maintain their structural integrity after implantation (e.g., about 80% of original strength) for a period of time, depending on the various processing parameter and the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

For non-absorbable barbed wound closure devices constructed in accordance with the present disclosure, suitable non-absorbable materials which may be utilized to form the wound closure device include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; fluoropolymers such as polytetrafluoroethylene; polyether-esters such as polybutesters; polytetramethylene ether glycol; 1,4-butanediol; polyurethanes; and combinations thereof. In other embodiments, non-absorbable materials may include silk, cotton, linen, carbon fibers, and the like. The polypropylene can be isotactic polypropylene or a mixture of isotactic and syndiotactic or atactic polypropylene.

The wound closure devices in accordance with the present disclosure may be coated or impregnated with one or more synthetic or natural polymers e.g., bioactive agents which accelerate or beneficially modify the healing process when the wound closure device is applied to a wound or surgical site. In particular embodiments, a bioactive agent may be solely disposed within the angle between the barb and the elongate body. Placement of a bioactive agent in the angle formed between the barbs and the elongate body surface places the bioactive agent at precisely defined locations within a tissue wound closure, thereby providing a unique controlled and sustained release dosage form (as opposed to coating entire wound closure device with a bioactive agent)

In certain embodiments, the coating may be formed from absorbable polymers selected from the group consisting of lactones, carbonates, polyorthoesters, hydroxyalkoanates, hydroxybutyrates, bioactive agents, polyanhydrides, silicone, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents that may be impregnated with or coated on the presently disclosed wound closure devices include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents that may be impregnated with or coated on the presently disclosed wound closure devices include substances which are beneficial to the animal and tend to promote the healing process. For example, a wound closure device can be provided with a bioactive agent that will be deposited at the surgical site. The bioactive agent can be chosen for its antimicrobial properties, capability for promoting wound repair and/or tissue growth, or for specific indications such as thrombosis.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, monoclonal antibody and polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily impregnated with or coated on the presently disclosed wound closure devices. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, α,α-dipyridyl, β-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be impregnated with or coated on the presently disclosed wound closure devices. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

The wound closure devices in accordance with this disclosure can also include, for example, biologically acceptable plasticizers, antioxidants and colorants, which can be impregnated into the barbs of the present disclosure or included in a coating thereon.

Bioactive agents may be applied onto a barbed wound closure device of the present disclosure utilizing any method within the purview of one skilled in the art including, for example, dipping, spraying, vapor deposition, brushing, mixing, compounding and the like.

The wound closure devices of the present disclosure may contain additives such as dyes, pigments, and colorants in order to increase the visibility of the device in the surgical field. Any suitable agent such as those agents within the purview of those skilled in the art can be used in accordance with the present disclosure.

The wound closure devices of the present disclosure may be utilized in any cosmetic, endoscopic or laparoscopic methods.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A wound closure device, comprising:
   an elongated body having first and second sections, the sections being configured and dimensioned for insertion within tissue on opposed sides of a wound;
   a depth stop positioned on the elongated body to limit an insertion depth of at least a portion of the elongated body within tissue; and
   at least one barb extending radially outward from the elongated body, the at least one barb including a distal tip and being movable between first and second positions, wherein in the first position, the distal tip is in close cooperative alignment with the elongated body, and in the second position, the distal tip is radially offset from the elongated body,
   wherein the at least one barb defines an inner surface having a first portion disposed at a first orientation relative to a longitudinal axis of the elongated body and a second portion disposed at a second orientation relative to the longitudinal axis,
   wherein the inner surface further includes a third portion disposed at a third orientation relative to the longitudinal axis,
   wherein at least one of the first, second, and third portions is substantially linear, wherein the first, second, and third portions are at first, second, and third angles relative to respective longitudinal axes of the elongated body,
wherein the second angle is less than each of the first and third angles,
wherein the at least one barb includes a first barb being formed of a first material and a second barb being formed of a second material different than the first material, one of the first or second materials having either more flexibility or more rigidity than the other of the first and second materials.

2. The wound closure device according to claim 1, wherein the first angle is about 0 degrees to about 90 degrees.

3. The wound closure device according to claim 1, wherein the first angle is about 30 degrees to about 40 degrees.

4. The wound closure device according to claim 1, wherein the second angle is about 0 degrees to about 90 degrees.

5. The wound closure device according to claim 1, wherein the second angle is about 2 degrees to about 10 degrees.

6. The wound closure device according to claim 1, wherein the third angle is about 0 degrees to about 90 degrees.

7. The wound closure device according to claim 1, wherein the third angle is about 25 degrees to about 50 degrees.

8. The wound closure device according to claim 1, wherein at least one of the first, second, and third portions is substantially non-linear.

9. The wound closure device according to claim 1, wherein at least one of the first, second, and third portions is arcuate.

10. The wound closure device according to claim 1, wherein the elongated body includes a plurality of barbs formed along at least a portion of a length thereof.

11. The wound closure device of claim 1, wherein the depth stop bisects the elongated body at a center of the elongated body, the depth stop defining a maximum diameter of the wound closure device at the center of the elongated body.

12. A wound closure device, comprising:
an elongated body having first and second sections, the sections being configured and dimensioned for insertion within tissue on opposed sides of a wound;
a depth stop that bisects the elongated body to define the first and second sections of the elongated body; and
first and second barbs extending substantially radially outwardly from the elongated body, wherein one of the first and second barbs has either more flexibility or more rigidity than the other of the first and second barbs, the first barb being formed of a first material and the second barb being formed of a second material different than the first material, one of the first or second materials having either more flexibility or more rigidity than the other of the first and second materials.

13. The wound closure device according to claim 12, wherein the first and second barbs have different geometries.

14. The wound closure device according to claim 12, wherein the first and second barbs have different thicknesses.

15. The wound closure device according to claim 12, wherein at least one of the first and second barbs has at least one surface treatment.

16. The wound closure device of claim 12, wherein at least one of the barbs extends radially outward from the elongated body and includes a distal tip, the at least one barb being movable between first and second positions, wherein in the first position, the distal tip is in close cooperative alignment with the elongated body, and in the second position, the distal tip is radially offset from the elongated body.

17. The wound closure device of claim 12, wherein the elongated body has a stepped configuration.

18. A wound closure device, comprising:
an elongated body having first and second sections, the sections being configured and dimensioned for insertion within tissue on opposed sides of a wound;
a depth stop that bisects the elongated body to define the first and second sections of the elongated body; and
first and second barbs extending substantially radially outwardly from the elongated body, wherein one of the first and second barbs has either more flexibility or more rigidity than the other of the first and second barbs, at least one of the first and second barbs having additional cross-linking.

19. The wound closure device of claim 18, wherein at least one of the barbs extends radially outward from the elongated body and includes a distal tip, the at least one barb being movable between first and second positions, wherein in the first position, the distal tip is in close cooperative alignment with the elongated body, and in the second position, the distal tip is radially offset from the elongated body.

20. The wound closure device of claim 18, wherein the depth stop defines a maximum diameter of the wound closure device at a center of the elongated body where the depth stop bisects the elongated body.

* * * * *